(12) United States Patent
Lin (10) Patent No.: US 10,668,026 B2
(45) Date of Patent: Jun. 2, 2020

(54) HAIR GROWTH STIMULATING DRESSING

(71) Applicant: NATIONAL TAIWAN OCEAN UNIVERSITY, Keelung (TW)

(72) Inventor: Hsiu-Mei Lin, Keelung (TW)

(73) Assignee: National Taiwan Ocean University (TW)

(*) Notice: Subject to any disclaimer, the term of this patent is extended or adjusted under 35 U.S.C. 154(b) by 198 days.

(21) Appl. No.: 15/886,837

(22) Filed: Feb. 2, 2018

(65) Prior Publication Data
US 2019/0240165 A1   Aug. 8, 2019

(51) Int. Cl.
| | |
|---|---|
| *A61K 9/70* | (2006.01) |
| *A61Q 7/00* | (2006.01) |
| *A61K 8/02* | (2006.01) |
| *A61K 8/25* | (2006.01) |
| *A61K 33/24* | (2019.01) |
| *A61K 8/19* | (2006.01) |
| *A61F 13/12* | (2006.01) |
| *A61K 33/244* | (2019.01) |

(52) U.S. Cl.
CPC ............... *A61K 9/703* (2013.01); *A61F 13/12* (2013.01); *A61K 8/0204* (2013.01); *A61K 8/0208* (2013.01); *A61K 8/19* (2013.01); *A61K 8/25* (2013.01); *A61K 33/24* (2013.01); *A61K 33/244* (2019.01); *A61Q 7/00* (2013.01)

(58) Field of Classification Search
CPC ........ A61K 33/24; A61K 8/0204; A61K 8/25; A61K 9/703; A61Q 7/00
See application file for complete search history.

(56) References Cited

FOREIGN PATENT DOCUMENTS

CN         106693059    *  5/2017   ........... A61F 2/0063

OTHER PUBLICATIONS

Mehrasa et al. (Materials Science & Engineering C; 2016) (Year: 2016).*
Gnanasammandham et al. (Nature Protocols, vol. 11 No. 4, 2016, 689-713) (Year: 2016).*

* cited by examiner

*Primary Examiner* — Anna R Falkowitz (57) ABSTRACT

The present invention discloses a hair growth stimulating dressing having advantages of simple manufacturing processes, low manufacture cost and reasonable selling price. To fabricate the hair growth stimulating dressing, it is firstly took mesoporous silica nanoparticles doped with lanthanide elements and at least one polymer matrix as raw materials to fabricate a plurality of biological fibers; and subsequently, the biological fibers are weaved to a biological textile. Particularly, the hair growth stimulating dressing can indeed show a promotion effect of hair growth on the heads of BALB/c nude mice after being covered onto the head of the nude mice. Therefore, compared to the fact that the commercial hair growth promoting products only just can show apparent hair growing effect on user's head after being continuously used for at least 4 months, this hair growth stimulating dressing only takes 7 days to exhibit positive hair growing effect on user's head.

9 Claims, 13 Drawing Sheets

HAIR GROWTH STIMULATING DRESSING

BACKGROUND OF THE INVENTION

1. Field of the Invention

The present invention relates to the field of modern biotechnologies, and more particularly to a hair growth stimulating dressing.

2. Description of the Prior Art

It has been known that causes of hair loss include genetic factor, environmental factor and pathological physiological state induced by stress of life, and most of the middle-aged men have the hair loss trouble nowadays.

At present, there are many products for promoting hair growth on sale, such as Rogaine and Propecia. However, despite the fact that Rogaine has been clinically proved showing positive effect on the promotion of hair growth for men, there are almost half of the men can merely get a few fine and thin short hairs on their head after being treated with Rogaine. On the other hand, the hair growing effect resulted from Propecia is found to obviously decline after the men use Propecia for 1 year. Before starting to use these hair growth promoting products, introductions or information about the possible adverse effects brought by the hair growth promoting products should be fully received. For instance, Rogaine has the adverse effects of scalp itching, visual disturbance, chest pain, low blood pressure, low sexual desire, etc. In addition, Propecia may cause the adverse effects of decreased libido, erectile dysfunction and ejaculation disorder in user's body.

On the other hand, owing to the fact that these commercial products for promoting hair growth are too expensive, the users having limited incomes have no will to buy it even if they are in the trouble of hair loss. From above descriptions, it is clear that how to develop a hair growth promoting product having advantages of simple manufacturing processes, low manufacture cost and reasonable selling price has become an important issue. In view of that, inventors of the present application have made great efforts to make inventive research thereon and eventually provided a hair growth stimulating dressing.

SUMMARY OF THE INVENTION

Differing from the fact that the commercial hair growth promoting products show drawbacks of complex ingredient composition and expensive selling price, the primary objective of the present invention is to disclose a hair growth stimulating dressing having advantages of simple manufacturing processes, low manufacture cost and reasonable selling price. To fabricate the hair growth stimulating dressing, it is firstly took mesoporous silica nanoparticles doped with lanthanide elements and at least one polymer matrix as raw materials to form a plurality of biological fibers through an electro-spinning equipment or a drawing apparatus; and subsequently, the plurality of biological fibers are weaved to a biological textile. Moreover, a variety of experimental data have proved that, the hair growth stimulating dressing can indeed show a promotion effect of hair growth on the heads of BALB/c nude mice after being covered on the head of the nude mice for a certain time. Therefore, compared to the fact that the commercial hair growth promoting products only just can show the hair growing effect on user's head after being continuously used for at least 4 months, this hair growth stimulating dressing only takes 7 days to exhibit a positive hair growing effect on user's head.

For achieving the primary objective of the present invention, the inventor of the present invention provides an embodiment for the hair growth stimulating dressing, which comprises a biological textile weaved by a plurality of biological fibers, wherein each of the plurality of biological fibers comprises:
a polymer sheath; and
a plurality of mesoporous silica nanoparticles doped with lanthanide elements, doped in or enclosed by the polymer sheath.

in order to achieve the primary objective of the present invention, the inventor of the present invention provides another one embodiment for the hair growth stimulating dressing, which comprises a biological textile weaved by a plurality of biological fibers and a plurality of fibers, wherein each of the plurality of biological fibers comprises:
a polymer sheath; and
a plurality of mesoporous silica nanoparticles doped with lanthanide elements, doped in or enclosed by the polymer sheath.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein.

DETAILED DESCRIPTION OF THE PREFERRED EMBODIMENTS

To more clearly describe a hair growth stimulating dressing according to the present invention, embodiments of the present invention will be described in detail with reference to the attached drawings hereinafter.

First Embodiment

Figure 1:
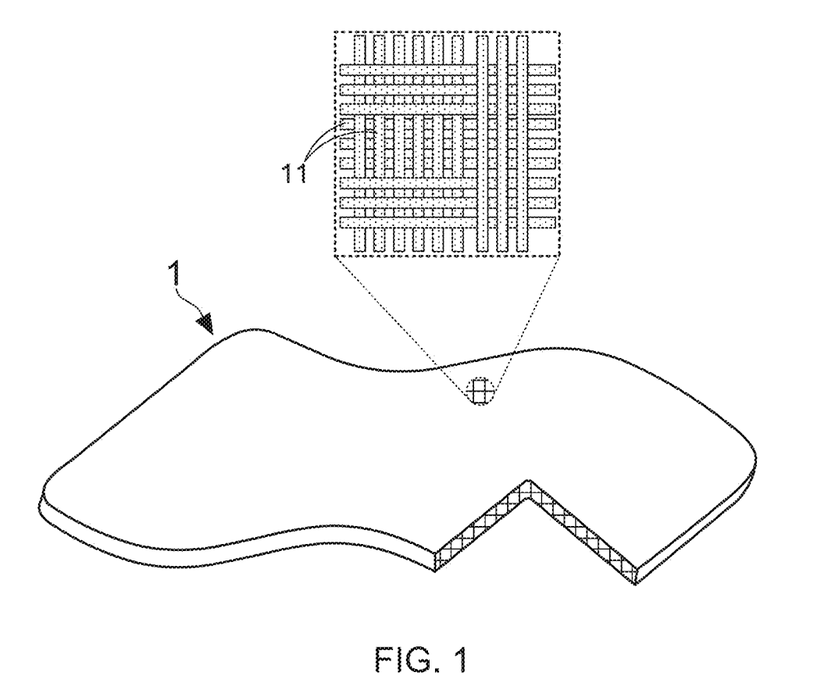
FIG. 1 shows a schematic stereo diagram of a first embodiment of a hair growth stimulating dressing according to the present invention.
Figure 2:
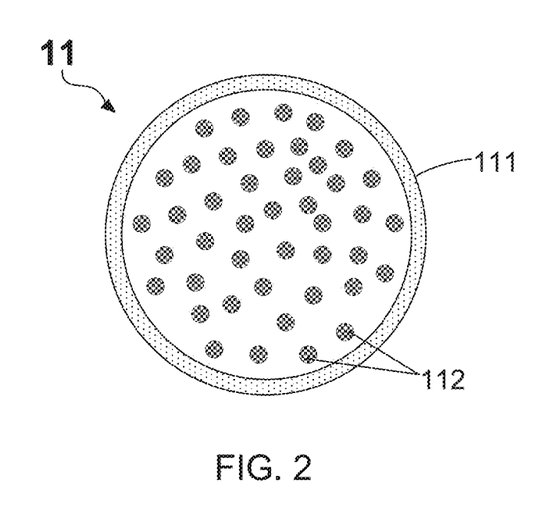
FIG. 2 shows a cross sectional side view of a biological fiber.

With reference to FIG. 1, there is provided a schematic stereo diagram of a first embodiment of a hair growth stimulating dressing according to the present invention. From FIG. 1, it is understood that the hair growth stimulating dressing 1 comprises a biological textile weaved by a plurality of biological fibers 11. Please simultaneously refer to FIG. 2, which illustrate a cross sectional side view of the biological fiber 11. As FIG. 2 shows, the biological fiber 11 comprises a polymer sheath 111 and a plurality of mesoporous silica nanoparticles (MSN particles) 112 doped with lanthanide elements. Particularly, the MSN particles 112 have a chemical formula of $SiO_2{}^x$:$Eu^y Gd^z$, and are doped in or enclosed by the polymer sheath 111. In the chemical formula, x is a value of weight percent in a range from 99 to 99.8. Moreover, y and z also present values of weight percent, and are both in a range between 0.1 and 0.5.

It needs to emphasize that the manufacturing material of the polymer sheath 111 does not be particularly limited in the present invention, which is selected from the group consisting of compound of gelatin and trifluoroethanol (TFE), compound of gelatin, TFE and polycaprolactone (PCL), compound of gelatin, TFE and polylactide (PLA), polyester, polyurethane (PU), polyvinyl chloride (PVC), polypropylene (PP), and polyamide (PA). Moreover, it is worth explaining that gelatin, PCL and PLA belong to biodegradable polymer materials, and the others are all synthesis polymer materials.

First Manufacturing Method

Before weaving the biological textile of the hair growth stimulating dressing 1, the MSN particles 112 must be firstly made according to the manufacturing flow comprising following steps:
(1) adding cetyltrimethylammonium bromide (CTAB) and NaOH into a beaker or any other one-opening container filled with distilled deionized (DD) water, and then heating and stirring the solution of the aforesaid materials; wherein the CTAB is used as a surfactant and the NaOH is known one kind of alkali metal hydroxide;
(2) sequentially adding tetraethyl orthosilicate (TEOS), europium(III) chloride ($EuCl_3$), and gadolinium(III) chloride into the solution obtained from the step (1), and stirring the solution of the aforesaid materials;
(3) applying a centrifuging treatment to the beaker, and then screening out precipitates from the solution in the beaker;
(4) drying the precipitates; and
(5) applying a calcination treatment to the dried precipitates, therefore the MSN particles 112 are obtained.

Figure 3A:
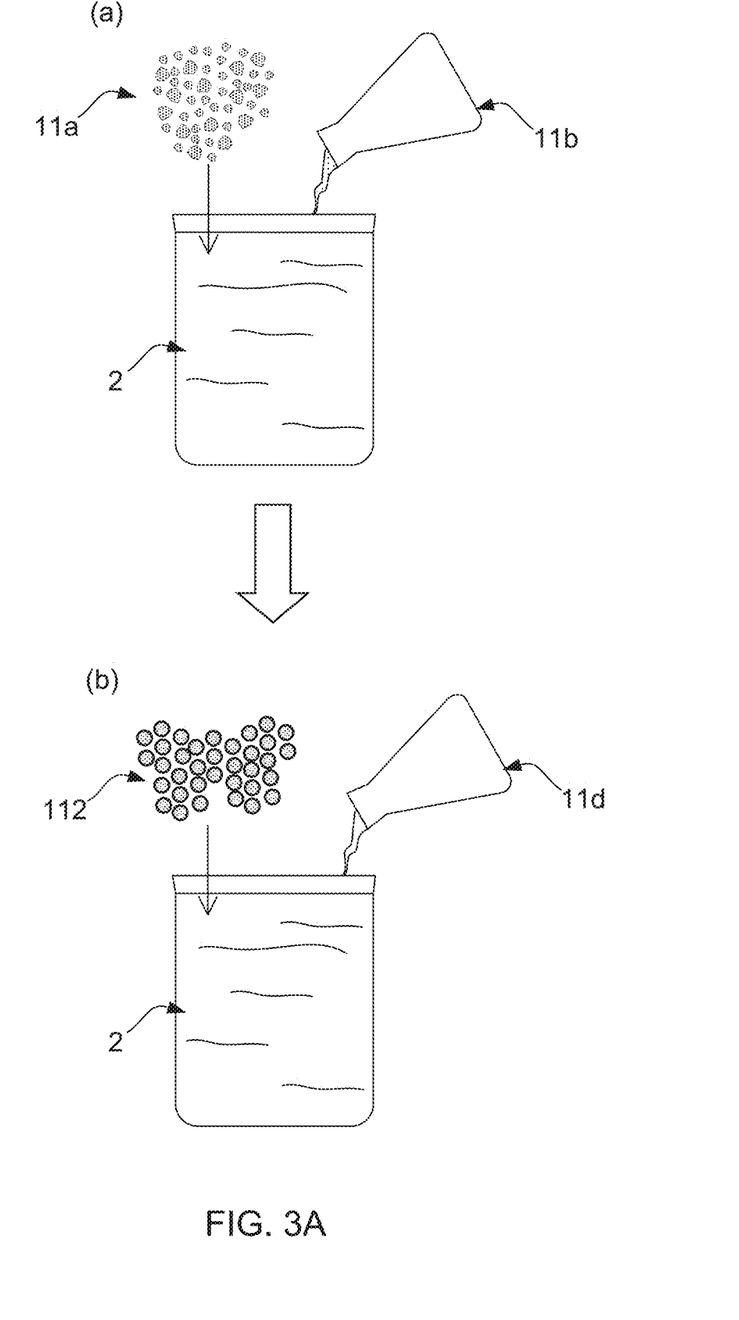
FIG. 3A and FIG. 3B show schematic diagrams for describing one manufacturing flow of the biological fibers.
Figure 3B:
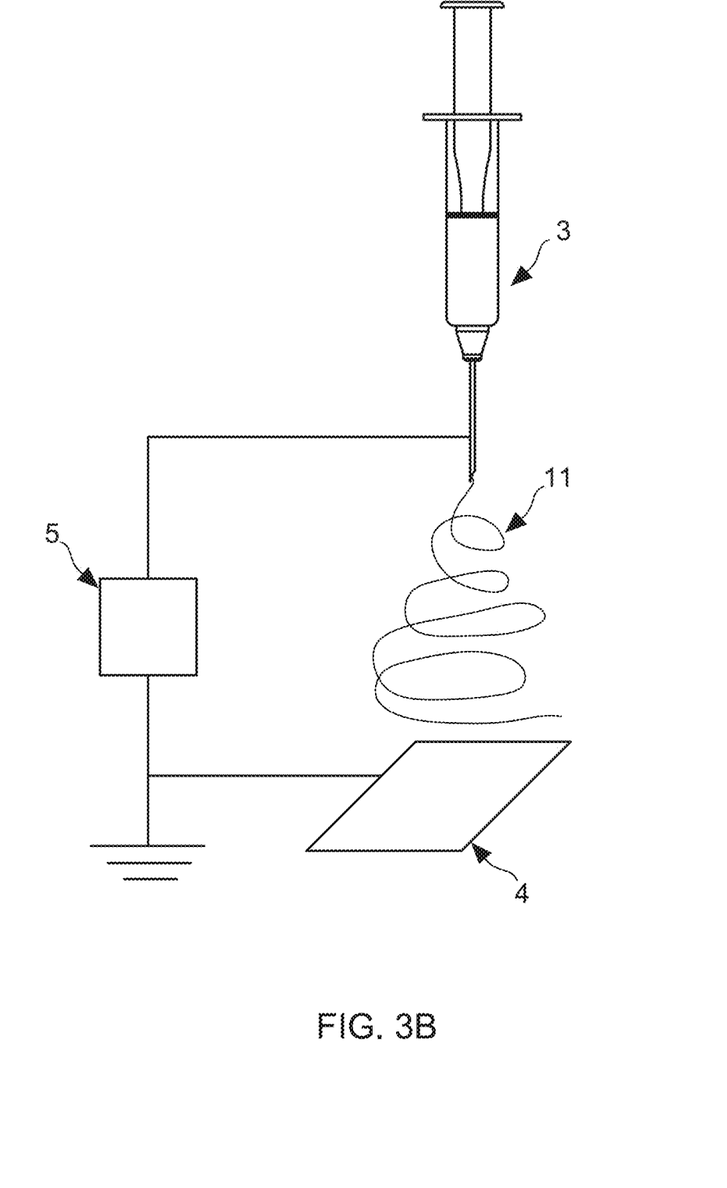

Particularly, the MSN particles 112 obtained from the step (5) have a chemical formula of $SiO_2{}^x$:$Eu^y Gd^z$. Subsequently, the MSN particles 112 and at least one polymer matrix can be token as raw materials to form a plurality of biological fibers 11 through an electro-spinning equipment or a drawing apparatus, wherein the manufacturing flow of the biological fibers 11 are provided in FIG. 3A and FIG. 3B. Diagram (a) of FIG. 3A depicts that gelatin 11a and solvent 11b such as 2,2,2-Trifluoroethanol (TFE) are adding into a reaction bottle 2. Moreover, from diagram (b) of FIG. 3A, it is known that the MSN particles 112 and DD water are subsequently added into the reaction bottle 2. After that, the solution in the reaction bottle 2 is filled into an apparatus 3 for injecting biological fibers 11. From FIG. 3B, it is found that a collection device 4 is disposed below the fiber injecting apparatus 3, and a voltage generating device 5 is electrically connected to the fiber injecting apparatus 3 and the collection device 4. Engineers skilled in the operation of electro-spinning system normally know that, a plurality of biological fibers 11 would be collected by the collection device 4 after a high voltage is applied to the fiber injecting apparatus 3 for making the fiber injecting apparatus 3 inject the solution by a form of fine silks.

Figure 4:
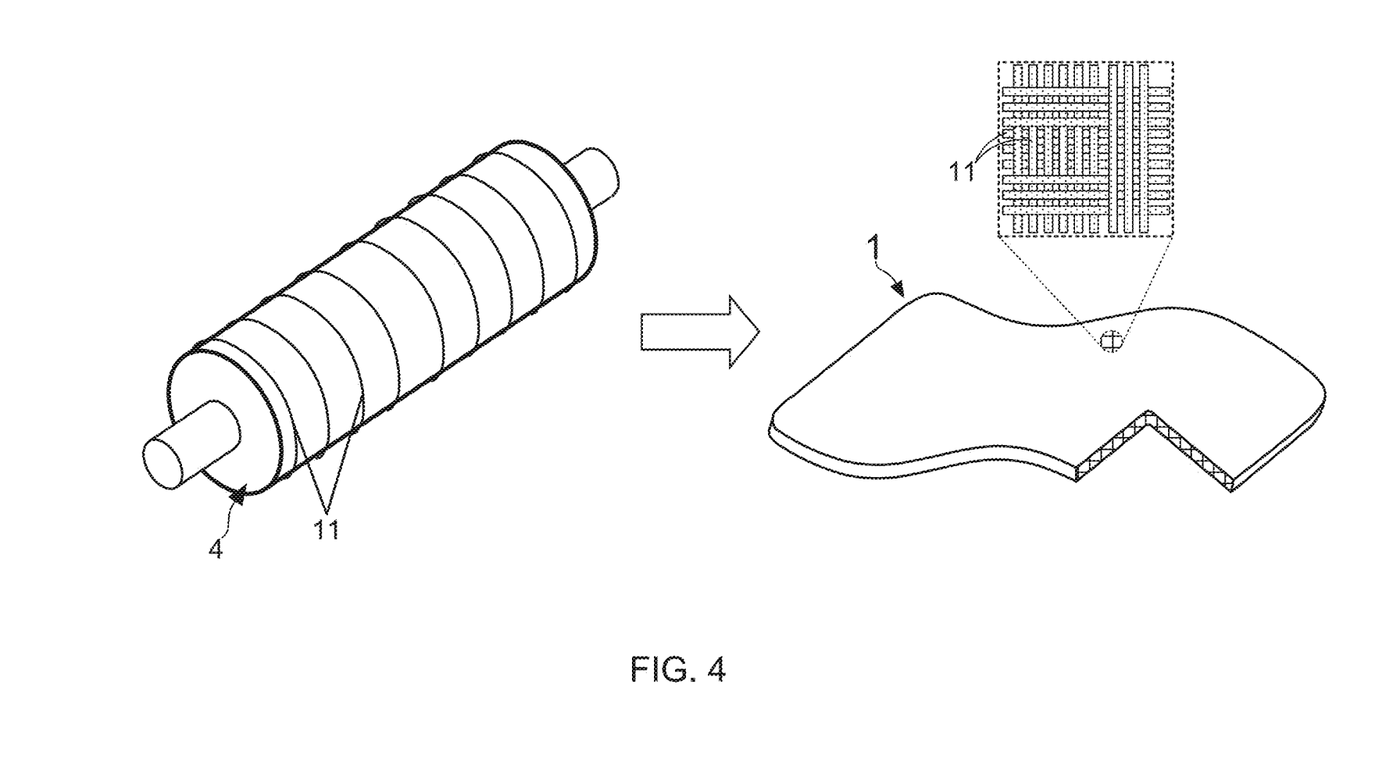
FIG. 4 shows schematic diagrams for describing another one manufacturing flow of the biological fibers.

Since the collection device 4 is a plate, the collected biological fibers 11 would be directly gathered to a biological textile of the hair growth stimulating dressing 1 proposed by the present invention. On the other hand, FIG. 4 shows schematic diagrams for describing another one manufacturing flow of the biological fibers. According to FIG. 4, it is known that the collection device 4 is a roller, and the biological fibers 11 are wound on the roller. Consequently, the biological fibers 11 on the roller can be further weaved to a biological textile of the hair growth stimulating dressing 1 by the use of weaving machine.

Second Manufacturing Method

Figure 5A:
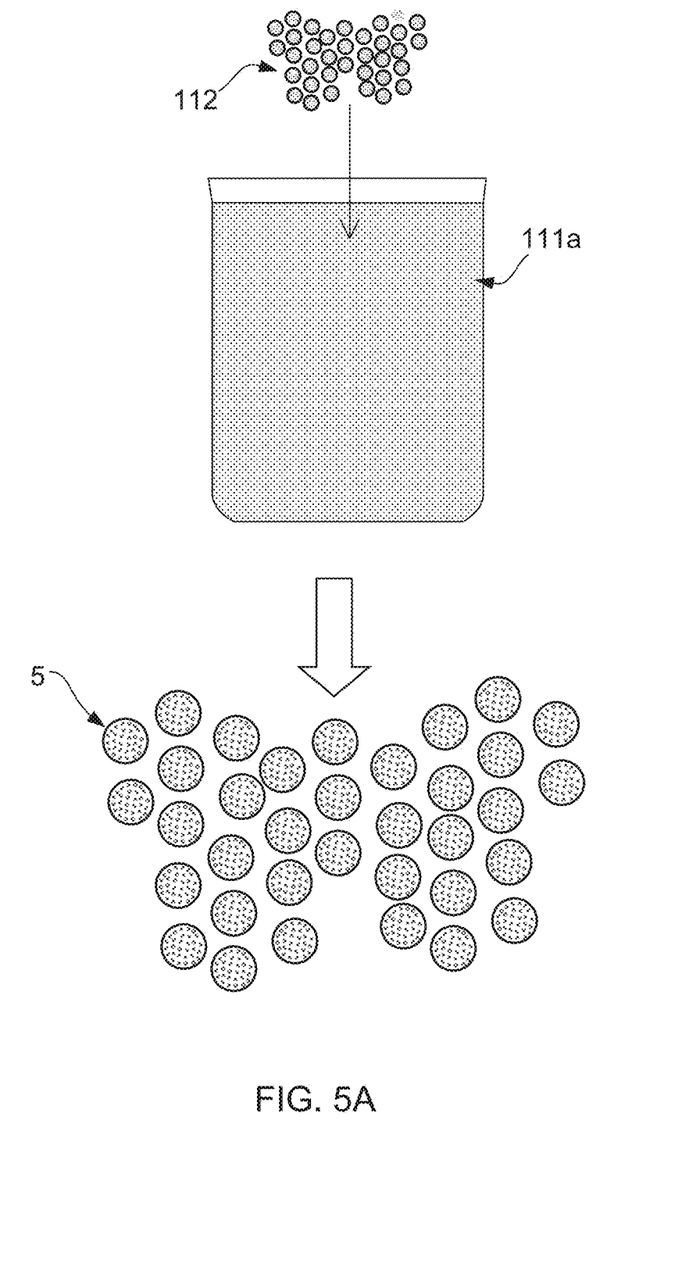
FIG. 5A, FIG. 5B and FIG. 5C show schematic diagrams for describing a manufacturing flow of the hair growth stimulating dressing.
Figure 5B:
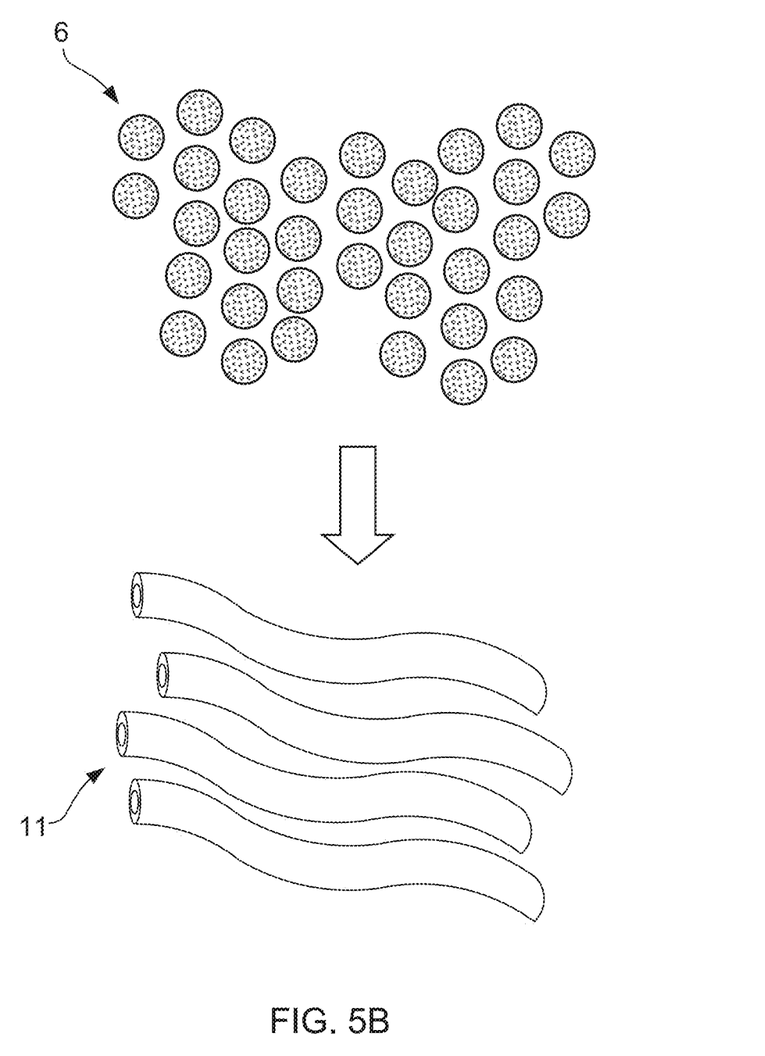
Figure 5C:
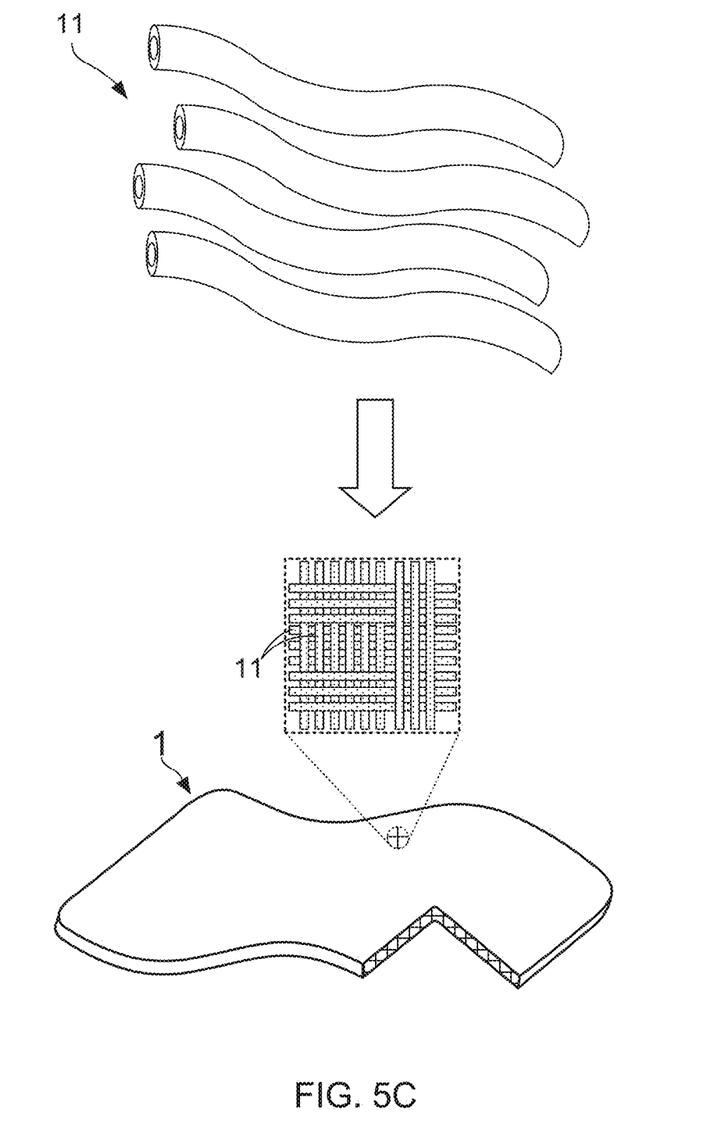

With reference to FIG. 5A, FIG. 5B and FIG. 5C, there are schematic diagrams provided for describing the manufacturing flow of the hair growth stimulating dressing. Differing from the above-introduced first manufacturing method, drawing apparatus is adopted for fabricating the biological fibers 11. As FIG. 5A shows, the MSN particles 112 are added into a monomer solution 111a, and the mixture of the aforesaid materials are further processed to a plurality of plastic masterbatches 6 after being sequentially applied with a polymerization treatment and a granulation treatment. FIG. 5B depicts that the plastic masterbatches 6 are subsequently processed to a plurality of biological fibers 11 by an drawing apparatus. Eventually, FIG. 5C shows that the biological fibers 11 are further weaved to a biological textile of the hair growth stimulating dressing 1 by the use of weaving machine.

Verification Experiment

For verifying whether the hair growth stimulating dressing 1 of the present invention can provide a promotion effect of hair growth on user's head, inventors of the present invention plan and subsequently complete a first embodiment. There are three nude mice (BALB/c, female) arranged in an experimental group, and the average body weight of the nude mice is 13 grams. For facilitating the hair growth stimulating dressing 1 able to be attached on the breech of the nude mice stably, a few DD water is dropped on the buttock of the nude mice before the hair growth stimulating dressing 1 is covered on the breech of the nude mice. It is worth explaining that the biological textile of the hair growth stimulating dressing 1 includes the MSN particles 112 with a dosage of 2.5 mg.

In the animal experiment, conversion between adult dose and animal dose of all test samples are carried out according to the guidance of estimating the maximum safe starting dose in initial clinical trials for therapeutics in adult healthy volunteer provided by U.S. Food and Drug Administration (USFDA). An easy formula for converting the adult dose to the animal dose is presented as follows: mouse equivalent dose per kilogram =(human equivalent dose per kilogram/60 kg)×12.3. Therefore, all of the equivalent doses for the nude mice are calculated and used.

Figure 6:
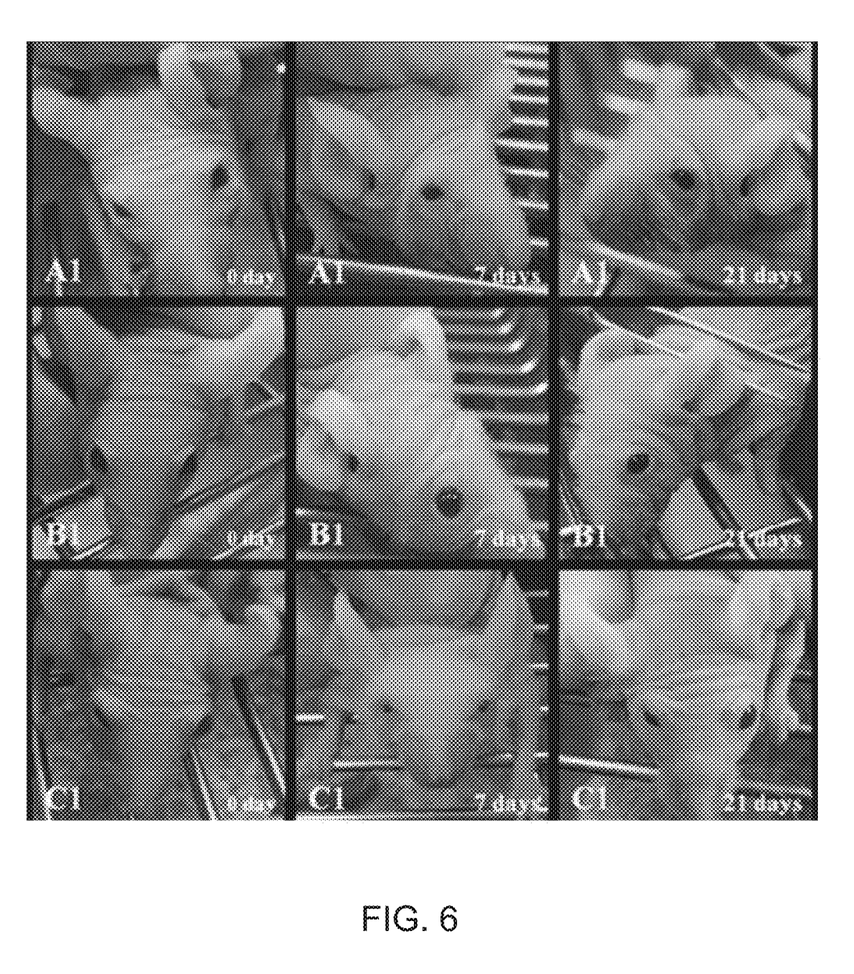
FIG. 6 shows image diagrams of BALB/c nude mice.

FIG. 6 shows image diagrams of the three nude mice respectively labeled with A1, B1 and C1. From data of FIG. 6, it is found that, the hair growing effect does exhibit on the head of mice A1 and B1 after the hair growth stimulating dressing is attached on their head for 7 days. It is worth noting that, the nude mice loss the grew hairs till 21 days passed. On the other hand, the hair growing effect does exhibit on the head of mouse C1 after the hair growth stimulating dressing is attached on their head for 12 days.

Figure 7:
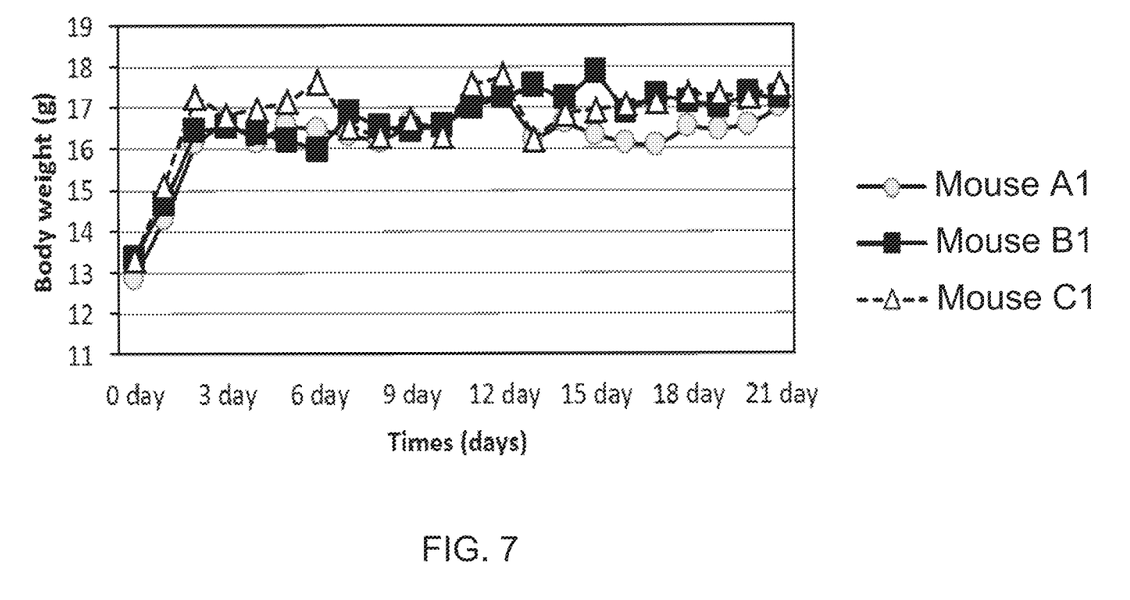
FIG. 7 shows graphic plot of time versus body weight.
Figure 8A:
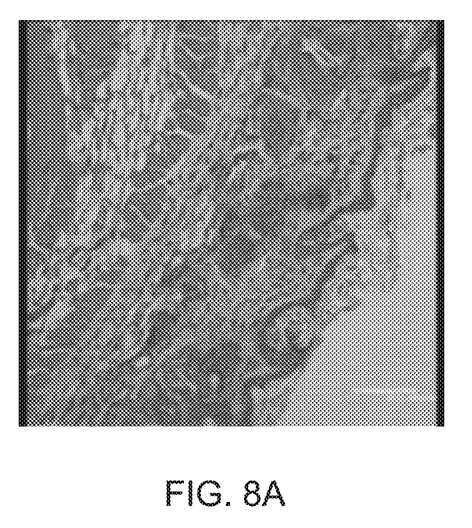
FIG. 8A shows an image diagram of a histologic section of the head of one BALB/c nude mouse selected from experimental group.
Figure 8B:
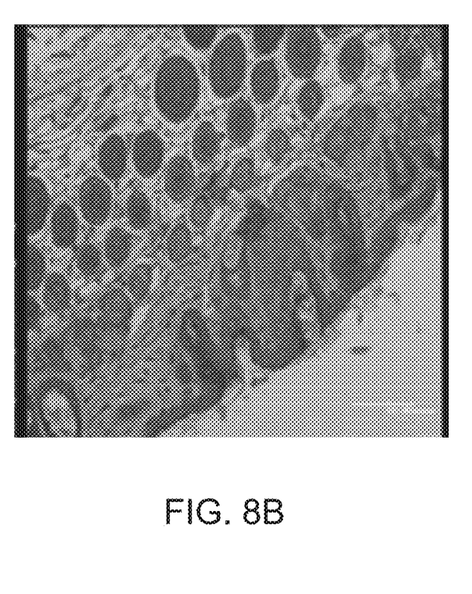
FIG. 8B shows an image diagram of a histologic section of the head of one BALB/c nude mouse selected from control group.

FIG. 7 shows graphic plot of time versus body weight. From data of FIG. 7, it is found that the body weight values of the nude mice do not obviously decline with the increasing of the use day of the hair growth stimulating dressing. On the other hand, FIG. 8A shows an image diagram of a histologic section of the head of one BALB/c nude mouse selected from experimental group. Moreover, FIG. 8B shows an image diagram of a histologic section of the head of one BALB/c nude mouse selected from control group. It needs to explain that the nude mice in control group do not provided the hair growth stimulating dressing on the head thereof. After comparing the data provided by FIG. 8A with the data shown in FIG. 8B, it is able to know that the nude mouse provided with the hair growth stimulating dressing on its head does not suffer from damage or inflammation of head skin tissue; moreover, there are no apparent discrepancies between the head skin tissue of the nude mouse in the experimental group and that of the nude mouse belonging to the control group. As a result, experimental data of FIG. 7, FIG. 8A and FIG. 8B have proved that, the hair growth stimulating dressing 1 of the present invention would not cause any adverse effects or induce toxic reactions in organisms.

Second Embodiment

Figure 9:
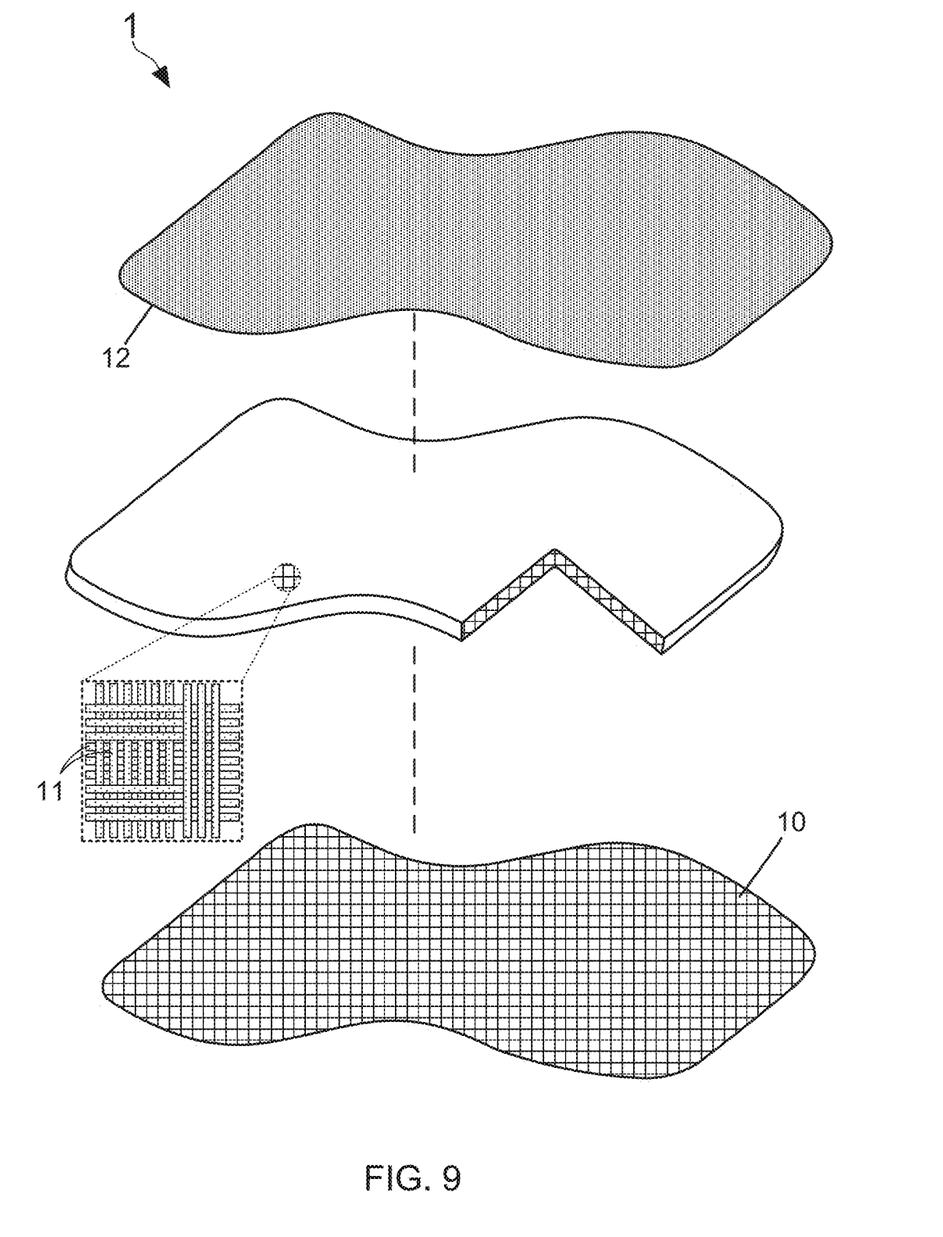
FIG. 9 shows a schematic stereo diagram of a second embodiment of the hair growth stimulating dressing.

With reference to FIG. 9, there is provided a schematic stereo diagram of a second embodiment of the hair growth stimulating dressing. After comparing FIG. 9 with FIG. 1, it is understood that the second embodiment of the hair growth stimulating dressing further comprises a substrate 10 for supporting the biological textile and an adhesive layer 12 formed on the biological textile.

Third Embodiment

Figure 10:
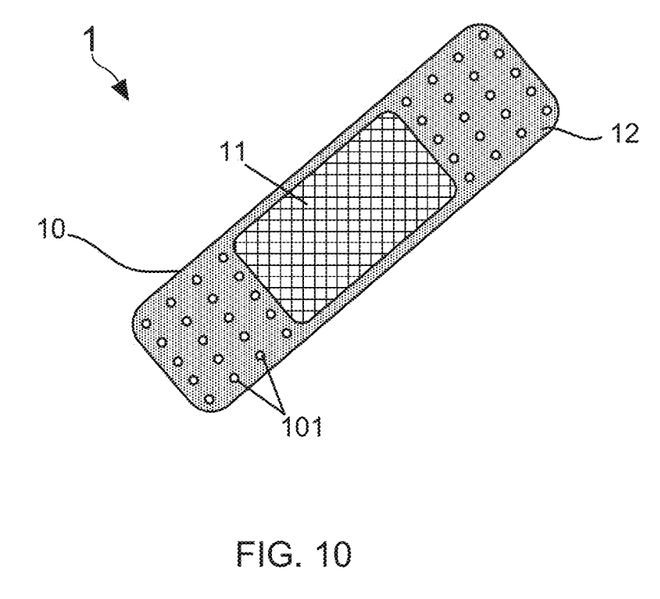
FIG. 10 shows a schematic stereo diagram of a third embodiment of the hair growth stimulating dressing.

With reference to FIG. 10, there is provided a schematic stereo diagram of a third embodiment of the hair growth stimulating dressing. In third embodiment, the hair growth stimulating dressing 1 is designed and then processed to an adhesive bandage, wherein the biological textile weaved by a plurality of biological fibers 11 is disposed on the substrate 10; moreover, the adhesive layer 12 is also disposed on the substrate 10. It is worth noting that, there are a plurality of air holes 101 formed on the substrate.

Fourth Embodiment

Figure 11:
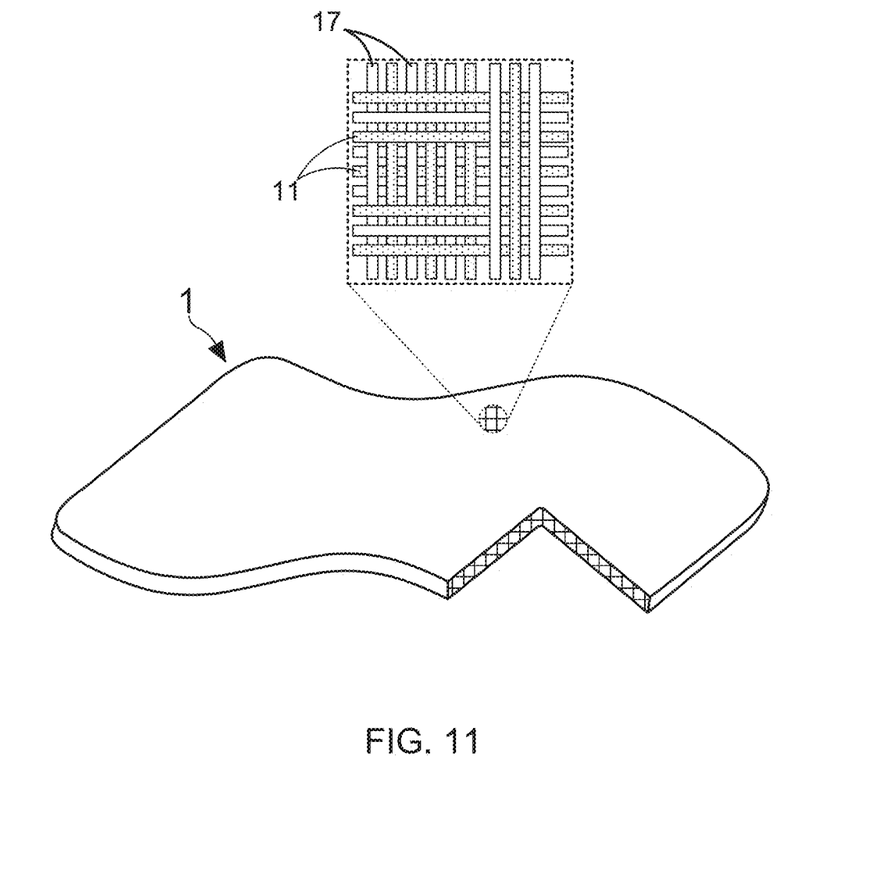
FIG. 11 shows a schematic stereo diagram of a fourth embodiment of the hair growth stimulating dressing.

With reference to FIG. 11, there is provided a schematic stereo diagram of a fourth embodiment of the hair growth stimulating dressing. In forth embodiment, the said biological textile is weaved by a plurality of biological fibers 11 and a plurality of polymer fibers 17. The same as the constitution of the biological fiber 11 adopted in the first embodiment, the biological fiber 11 used in the second embodiment also consists of a polymer sheath 111 and a plurality of Mesoporous silica nanoparticles (MSN particles) 112. The MSN particles 112 have a chemical formula of $SiO_2^x$:$Eu^y Gd^z$, and are doped in or enclosed by the polymer sheath 111.

It needs to emphasize that the manufacturing material of the polymer fibers 17 does not be particularly limited in the present invention, which is selected from the group consisting of compound of gelatin and trifluoroethanol (TFE), compound of gelatin, TFE and polycaprolactone (PCL), compound of gelatin, TFE and polylactide (PLA), polyester, polyurethane (PU), polyvinyl chloride (PVC), polypropylene (PP), and polyamide (PA). It is worth explaining that, because the biological textile is weaved by biological fibers 11 and polymer fibers 17, the manufacture cost of the fourth embodiment is lower than that of the first embodiment.

Therefore, through above descriptions, all embodiments and their constituting elements of the hair growth stimulating dressing proposed by the present invention have been introduced completely and clearly; in summary, the present invention includes the advantages of:

(1) Differing from the fact that the commercial hair growth promoting products exhibit drawbacks of complex ingredient composition and expensive selling price, the primary objective of the present invention is to disclose a hair growth stimulating dressing having advantages of simple manufacturing processes, low manufacture cost and reasonable selling price. To fabricate the hair growth stimulating dressing, it is firstly took mesoporous silica nanoparticles doped with lanthanide elements and at least one polymer matrix as raw materials to produce a plurality of biological fibers through an electro-spinning equipment or a drawing apparatus, and subsequently weaved the plurality of biological fibers to a biological textile. Moreover, a variety of experimental data have proved that, the hair growth stimulating dressing can indeed show a promotion effect of hair growth on the heads of BALB/c nude mice after being covered on the head of the nude mice for a certain time. Therefore, compared to the fact that the commercial hair growth promoting products only just can show apparent hair growing effect on user's head after being continuously used for at least 4 months, this hair growth stimulating dressing only takes 7 days to exhibit a positive hair growing effect on user's head The above description is made on embodiments of the present invention. However, the embodiments are not intended to limit scope of the present invention, and all equivalent implementations or alterations within the spirit of the present invention still fall within the scope of the present invention.

What is claimed is:

1. A hair growth stimulating dressing, comprising a biological textile weaved by a plurality of biological fibers, wherein each of the plurality of biological fibers comprises:
    a polymer sheath; and
    a plurality of nanoparticles, being doped in or enclosed by the polymer sheath;
    wherein the forgoing nanoparticle has a chemical formula $SiO_2^x Eu^y Gd^z$;
    wherein x is a first weight percent in a range between 99 and 99.8, y being a second weight percent in a range from 0.1 to 0.5, and z being a third weight percent in a range between 0.1 and 0.5; and
    wherein an amount of the plurality of nanoparticles that are contained in the hair growth stimulating dressing is 2.5 mg.

2. The hair growth stimulating dressing of claim 1, further comprising:
    a substrate for supporting the biological textile; and
    an adhesive layer, being formed on the biological textile.

3. The hair growth stimulating dressing of claim 1, wherein the manufacturing material of the polymer sheath is selected from the group consisting of compound of gelatin and trifluoroethanol (TFE), compound of gelatin, TFE and polycaprolactone (PCL), compound of gelatin, TFE and polylactide (PLA), polyester, polyurethane (PU), polyvinyl chloride (PVC), polypropylene (PP), and polyamide (PA).

4. The hair growth stimulating dressing of claim 2, wherein the substrate is provided with a glue layer thereon.

5. The hair growth stimulating dressing of claim 2, wherein there are a plurality of air holes formed on the substrate.

6. A hair growth stimulating dressing, comprising a biological textile weaved by a plurality of biological fibers and a plurality of fibers, wherein each of the plurality of biological fibers comprises:
a polymer sheath; and
a plurality of nanoparticles, being doped in or enclosed by the polymer sheath;
wherein the forgoing nanoparticle has a chemical formula $SiO_2{}^xEu^yGd^z$;
wherein x is a first weight percent in a range between 99 and 99.8, y being a second weight percent in a range from 0.1 to 0.5, and z being a third weight percent in a range between 0.1 and 0.5; and
wherein an amount of the plurality of nanoparticles that are contained in the hair growth stimulating dressing is 2.5 mg.

7. The hair growth stimulating dressing of claim 6, further comprising:
a substrate for supporting the biological textile; and
an adhesive layer, being formed on the biological textile.

8. The hair growth stimulating dressing of claim 6, wherein the manufacturing material of the polymer sheath is selected from the group consisting of compound of gelatin and trifluoroethanol (TFE), compound of gelatin, TFE and polycaprolactone (PCL), compound of gelatin, TFE and polylactide (PLA), polyester, polyurethane (PU), polyvinyl chloride (PVC), polypropylene (PP), and polyamide (PA).

9. The hair growth stimulating dressing of claim 6, wherein the manufacturing material of the sheath is selected from the group consisting of compound of gelatin and trifluoroethanol (TFE), compound of gelatin, TFE and polycaprolactone (PCL), compound of gelatin, TFE and polylactide (PLA), polyester, polyurethane (PU), polyvinyl chloride (PVC), polypropylene (PP), and polyamide (PA).

* * * * *